United States Patent
Xie et al.

(10) Patent No.: US 11,248,321 B2
(45) Date of Patent: Feb. 15, 2022

(54) PERFORATED NON-WOVEN FABRIC AND ITS MANUFACTURING METHOD

(71) Applicant: XIAMEN YANJAN NEW MATERIAL CO., LTD., Xiamen (CN)

(72) Inventors: Jihua Xie, Xiamen (CN); Jixiang Cai, Xiamen (CN); Jielong Luo, Xiamen (CN)

(73) Assignee: XIAMEN YANJAN NEW MATERIAL CO., LTD., Xiamen (CN)

(*) Notice: Subject to any disclaimer, the term of this patent is extended or adjusted under 35 U.S.C. 154(b) by 375 days.

(21) Appl. No.: 16/095,126

(22) PCT Filed: Aug. 22, 2017

(86) PCT No.: PCT/CN2017/098482
§ 371 (c)(1),
(2) Date: Oct. 19, 2018

(87) PCT Pub. No.: WO2018/036480
PCT Pub. Date: Mar. 1, 2018

(65) Prior Publication Data
US 2019/0127896 A1 May 2, 2019

(30) Foreign Application Priority Data
Aug. 25, 2016 (CN) .......................... 201610724595.4

(51) Int. Cl.
*D04H 1/558* (2012.01)
*A61F 13/512* (2006.01)
(Continued)

(52) U.S. Cl.
CPC .......... *D04H 1/558* (2013.01); *A61F 13/512* (2013.01); *A61F 13/5121* (2013.01);
(Continued)

(58) Field of Classification Search
CPC .......... D04H 1/558; D04H 1/485; D04H 1/49; D04H 1/495; A61F 13/512;
(Continued)

(56) References Cited

U.S. PATENT DOCUMENTS

| 4,840,829 A | 6/1989 | Suzuki et al. |
| 2007/0023135 A1* | 2/2007 | Giacometti ............ D04H 13/00 156/252 |

(Continued)

FOREIGN PATENT DOCUMENTS

| CN | 1492751 A | 4/2004 |
| CN | 100434055 C | 11/2008 |

(Continued)

OTHER PUBLICATIONS

English Translation of JP2011062227, published Mar. 31, 2011.*
English translation of CN103806223, published May 21, 2014.*

*Primary Examiner* — Nathan E Durham
*Assistant Examiner* — Abby M Spatz
(74) *Attorney, Agent, or Firm* — Cooper Legal Group, LLC

(57) ABSTRACT

A perforated non-woven fabric having at least one fiber layer that has a plurality of through holes. The total area of the through holes accounts for 10~80% of the total area of the perforated non-woven fabric; the opening of the through holes is flat with the surface of the perforated non-woven fabric; and the density of through holes on the perforated non-woven fabric is $3/cm^2 \sim 100/cm^2$. The fiber density at the edge of each through hole is similar to or the same as the fiber density in other areas of the perforated non-woven fabric. The fiber surrounds the through hole, and only the surface of the fiber is bonded to each other.

8 Claims, 8 Drawing Sheets

(51) Int. Cl.
  *B26F 1/08*         (2006.01)
  *B26F 1/24*         (2006.01)
(52) U.S. Cl.
  CPC ............ *A61F 13/5126* (2013.01); *B26F 1/08* (2013.01); *B26F 1/24* (2013.01)
(58) Field of Classification Search
  CPC .... A61F 13/5121; A61F 13/5126; B26F 1/08; B26F 1/24; B26F 1/10; B32B 38/04; B32B 2038/042; B32B 2038/047
  USPC ........... 28/106; 156/250, 251, 252, 269, 270
  See application file for complete search history.

(56) References Cited

U.S. PATENT DOCUMENTS

| | | | |
|---|---|---|---|
| 2012/0282436 A1* | 11/2012 | Coe ........................... | B31F 1/07 428/131 |
| 2013/0158497 A1* | 6/2013 | Yamaguchi ............. | B32B 3/266 604/378 |
| 2013/0174379 A1* | 7/2013 | Ishino ...................... | D06B 5/08 19/98 |

FOREIGN PATENT DOCUMENTS

| | | | |
|---|---|---|---|
| CN | 103261503 | A | 8/2013 |
| CN | 103806223 | A | 5/2014 |
| CN | 104510575 | A | 4/2015 |
| CN | 106319763 | A | 1/2017 |
| CN | 205954263 | U | 2/2017 |

\* cited by examiner

PERFORATED NON-WOVEN FABRIC AND ITS MANUFACTURING METHOD

TECHNICAL FIELD

The invention belongs to the technical field of non-woven fabrics, in particular to a perforated non-woven fabric and its manufacturing method.

BACKGROUND TECHNIQUE

Hot air through non-woven fabrics are widely used in sanitary absorbent products such as physiological sanitary towels or diapers because of their soft, skin-friendly and smooth characteristics. In order to improve the permeability of non-woven fabrics, it usually opens holes on hot air through non-woven fabric, which not only accelerates the penetration rate of body fluid, but also enables the body fluid to reach the absorption layer quickly through the surface layer, and reduces the contact area with the human body during use.

The prior opening generally adopts a set of intermeshing needle rollers and concave rollers, and CN200410028483.2 describes that the opening method is to put the laminate between the first extrusion module and the second extrusion module, pressing, forming an opening, wherein the surface of the first extrusion module has a plurality of rows of perforating needles, and the second extrusion module has corresponding grooves, and the heated needles squeeze the fiber rows during operation and are under the action of heat, the fiber at the edge of the punching needle is melt-shaped, so that a filming region is formed on the inner surface of the opening, thereby forming an opening, and the hole shape is maintained by the filming region. The defect of this method is that although the filming region formed by the melting of the fiber is located on the inner surface of the opening, when it comes into contact with the skin, it still produces a grainy feeling, which affects the softness of the non-woven fabric; But if the filming area is not formed, it can reduce the sense of graininess and increase the softness, but the hole is not good, especially when the hole is close to the paper core tube after the reel, the hole is elongated and the difference between the inside and outside is larger, thus affecting the permeability and beauty of the non-woven fabric.

Another form of hole forming is punching holes, but the fiber is cut off on the edge of the hole to produce fiber breakage, it is easy to stimulate the skin, and the cut off non-woven fabrics parts can not be used again. If the hole density is large, it will cause great waste and low production.

CN201410084794.4 discloses a manufacturing method and a device for a disposable pore-forming hot air through non-woven fabric, and the manufacturing method is as follows: opening, combing, and combing the fibers into the oven through the card clothing belt, since the perforating needle is fixedly distributed on the outer surface of the conveyor belt, the hot air through non-woven fabric is formed while punching. However, in terms of feasibility, the conveyor belt cannot be seamlessly connected. Therefore, when the punching needle is fixed on the outer surface, there is an uneven position at the joint, which eventually causes the product to have continuous defects such as poor mesh surface.

SUMMARY OF THE INVENTION

One object of the invention is to overcome the defects of the prior art and provides a perforated non-woven fabric.

Another object of the invention is to provide a manufacturing method of the perforated non-woven fabric.

The specific technical scheme of the invention is as follows:

A perforated non-woven fabric, consisting of at least one fiber layer, has a plurality of through holes, the total area of the plurality of through holes accounts for 10~80% of the total area of the perforated non-woven fabric, and the opening of the plurality of through holes is flat with the surface of the perforated non-woven fabric, and the density of the plurality of through holes on the perforated non-woven fabric is $3/m^2$~$100/cm^2$, the fiber density at the edge of each through holes is similar to or the same as the fiber density in other areas of the perforated non-woven fabric, and the fiber surrounds the through hole only the surface of the fiber is bonded to each other.

In a preferred embodiment of the invention, the through hole is a circular through hole, a regular polygonal through hole or an irregular shaped through hole.

In one preferred embodiment of the invention, the opening of one side of the through holes coincides with the size of the opening of the other side.

In one preferred embodiment of the invention, the size of the opening on one side of the through holes is larger than that on the other side.

In one preferred embodiment of the invention, it has a concave part or a convex part.

In one preferred embodiment of the invention, the total area of the plurality of through holes accounts for 20-30% of the total area of the perforated non-woven fabric. The opening density is $20/cm^2$~$40/cm^2$.

A manufacturing method of the perforated non-woven fabric, which comprises the following steps:

(1) the fiber of hot air through non-woven fabric are carding into at least one layer of fiber web through an unpacking device and a loosening device;

(2) at least one layer of fiber web is sent to a circular web rotary drum type oven. The surface of the circular web rotary drum of the circular web rotary drum type oven has a mesh hole and a punching pin insert. The hot air of 130~200° C. in the circular web rotary drum type oven passes through the mesh hole and alternately through the fiber web and consolidates it, at the same time, the punching pin insert will penetrate the corresponding surface of the fiber web to form through holes, thereby forming the perforated non-woven fabric.

In one preferred embodiment of the invention, the punching pin insert is conical, cylindrical or pyramidal.

In one preferred embodiment of the invention, the circular web rotary drum is provided with a convex plug-in corresponding to the other areas, and the perforated non-woven fabric is provided with through holes and a concave part at one time of processing and forming.

In a preferred embodiment of the invention, the circular web rotary drum is provided with a number of grooves, and the perforated non-woven fabric is provided with through holes and a convex part at one time of processing and forming.

In a preferred embodiment of the invention, the fiber web is preheated to 90~100° C. by a preheating device, and then enters the circular web rotary drum type oven.

In one preferred embodiment of the invention, the preheating device is a preheating oven.

The beneficial effects of the invention are as follows:

1. The fiber density of the perforated non-woven fabrics of the present invention is similar or the same in the edge region of the through hole and the other regions, and the fibers of the edge region of the through holes are arranged around the through holes and only the surface layer of the fiber is bonded, so that the edge region of the through holes of the non woven fabric is not broken to form rigid breaks, or melted to form a dense fiber area or a filmed area, only the fibers surround the through holes, the fiber surface is melted and adhered to each other so that the softness of the non-woven fabric is not to be destroyed by the opening, which reduces the graininess caused by the opening.

2. Although the through holes of the perforated non-woven fabric are plane through holes, it does not increase in the thickness direction of the non-woven fabric, but because the punching needle has a cylinder, cone or pyramid structure, the hole formed can be a straight hole or a funnel shaped opening. It is beneficial to collect body fluid, speed up penetration speed, and form rapid infiltration channels.

DETAILED DESCRIPTION

The technical scheme of the present invention will be further described and described in combination with the accompanying drawings through specific embodiments.

Figure 1:
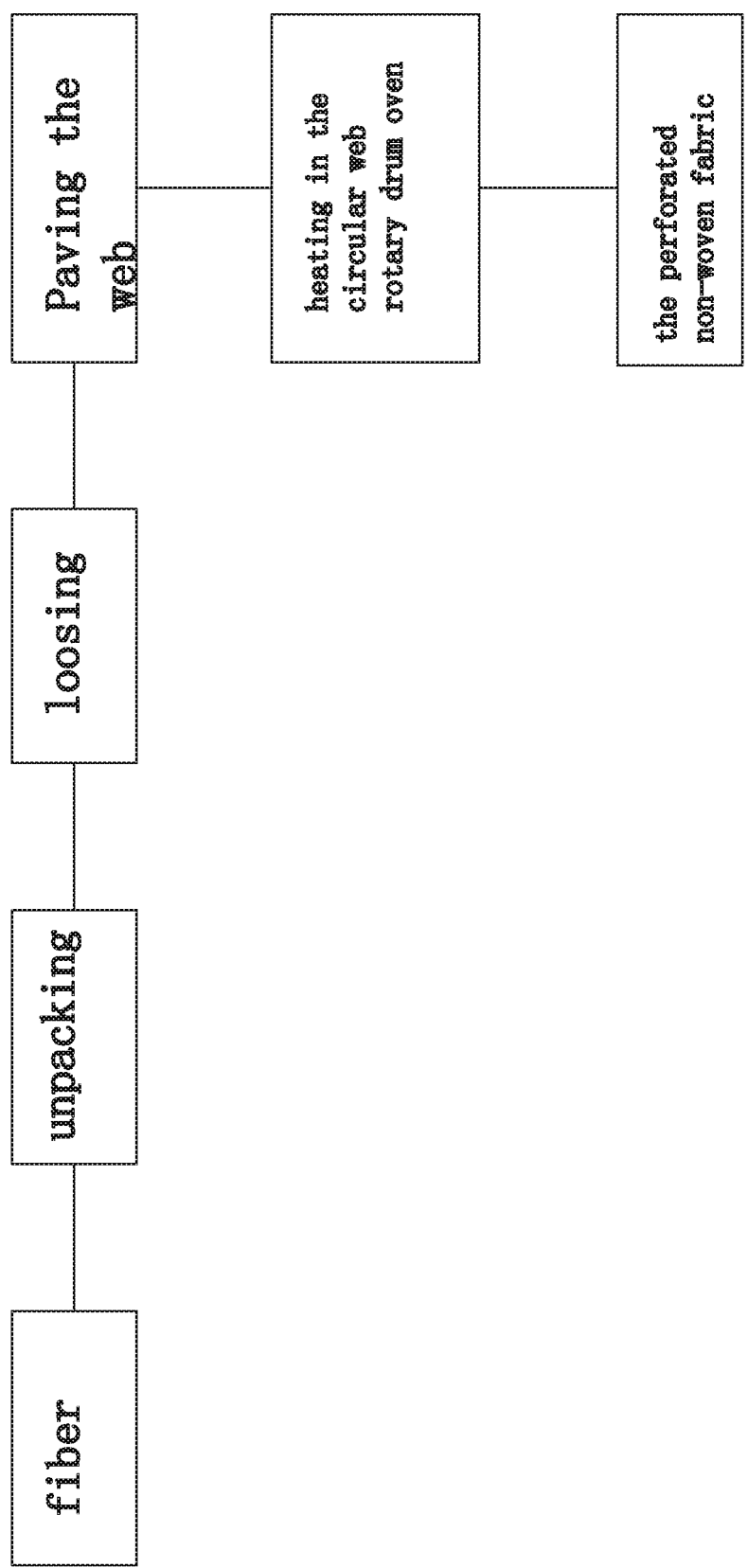
FIG. 1 is a flowchart for manufacturing the perforated non-woven fabric.
Figure 2:
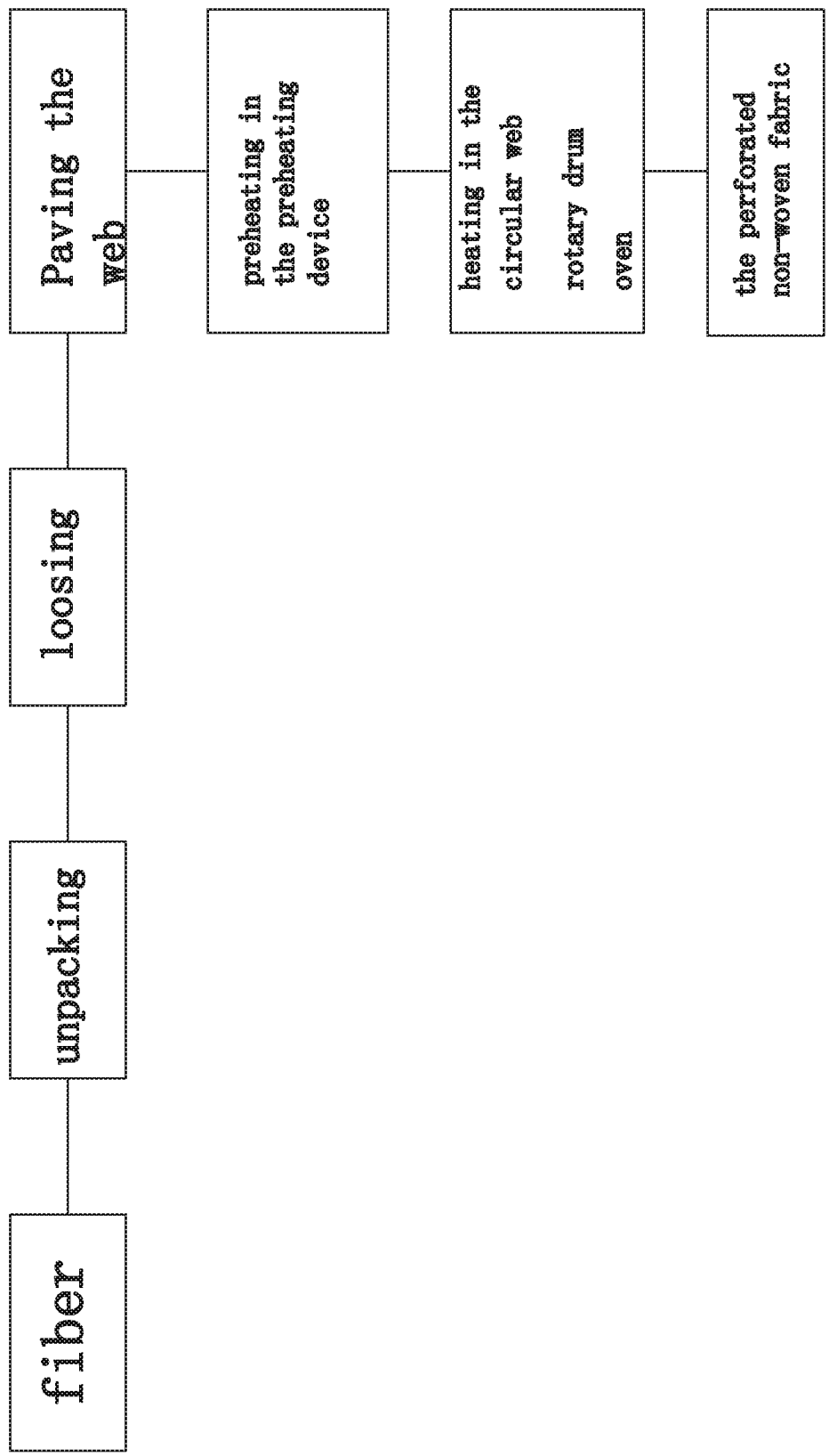
FIG. 2 is the flowchart of the perforated non-woven fabric with a preheating device.
Figure 3:
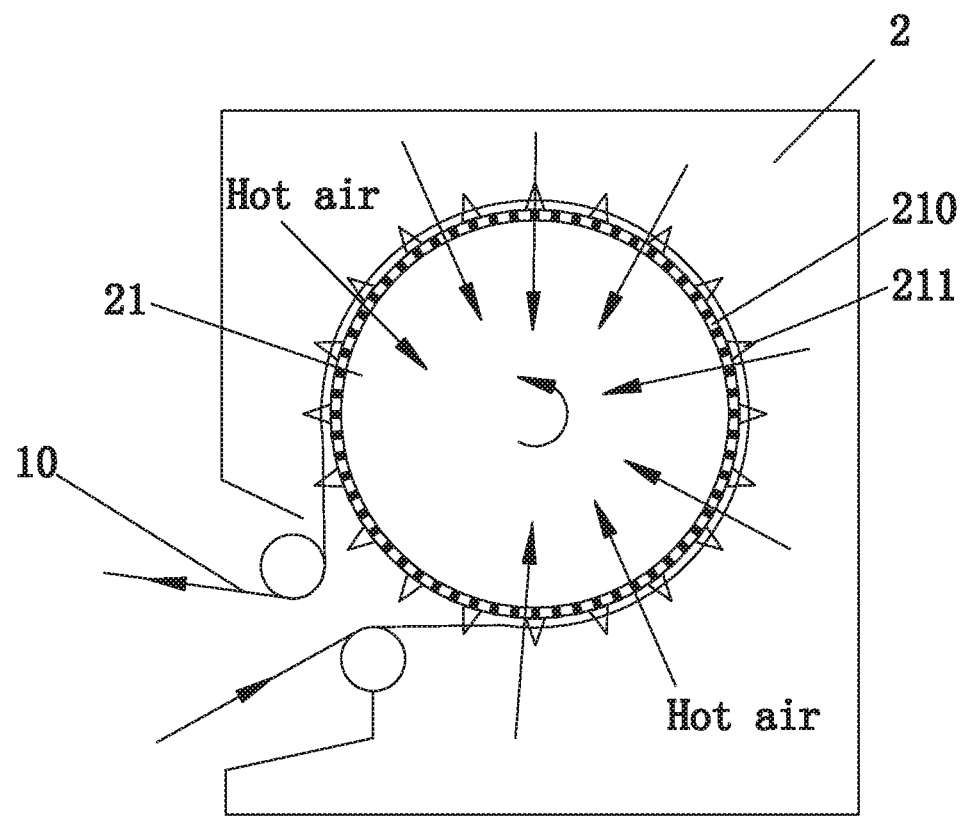
FIG. 3 is a schematic diagram of the forming method of a circular web oven.
Figure 4:
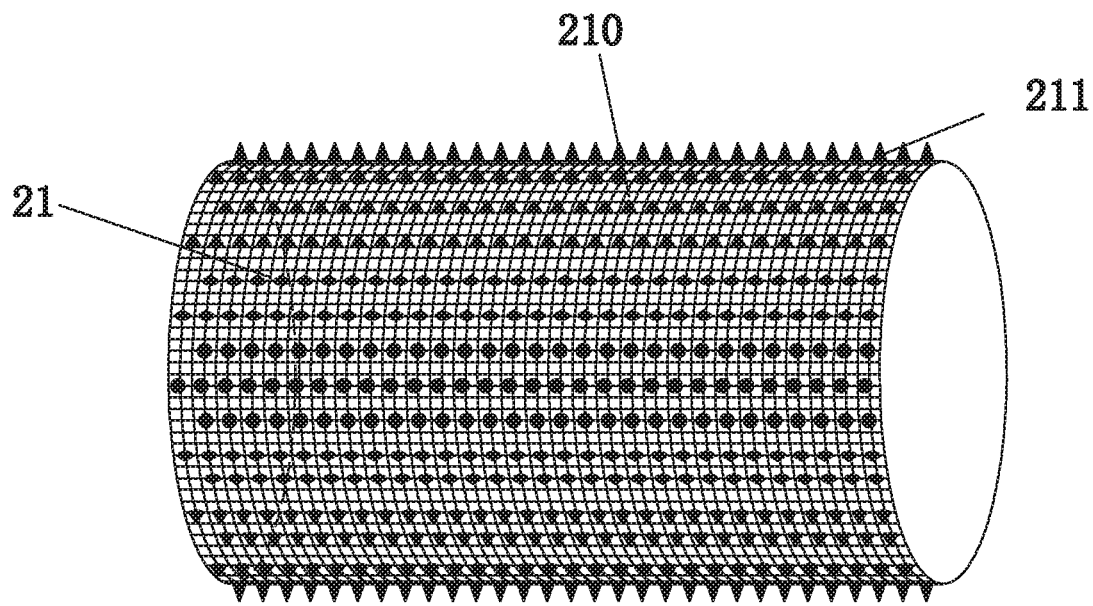
FIG. 4 is a schematic diagram of the circular web rotary drum.
Figure 5:
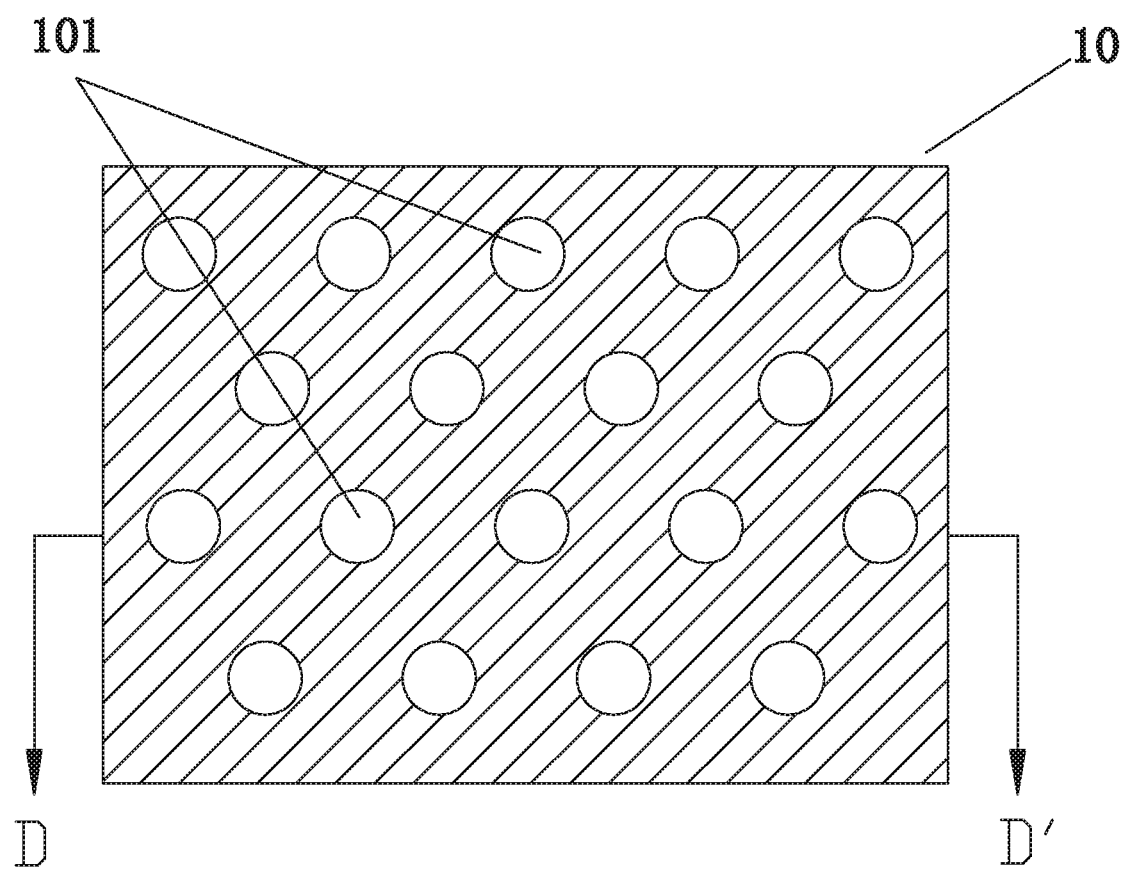
FIG. 5 is a top view of the perforated non-woven fabric of embodiment 1 of the present invention.
Figure 6:
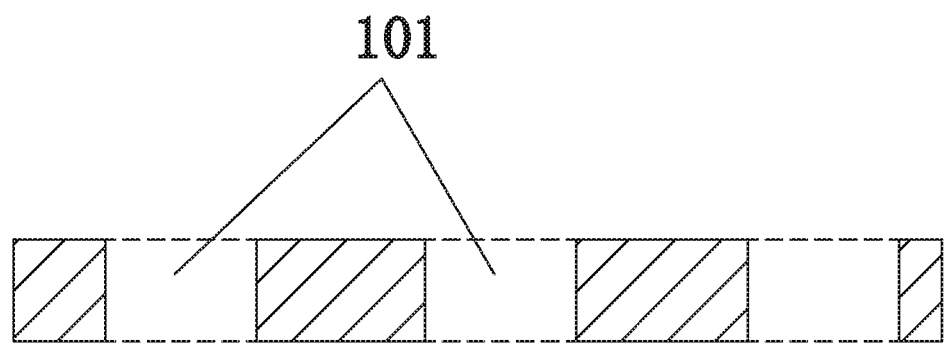
FIG. 6 is a cross-sectional view taken along the O-O' direction of FIG. 5.
Figure 7:
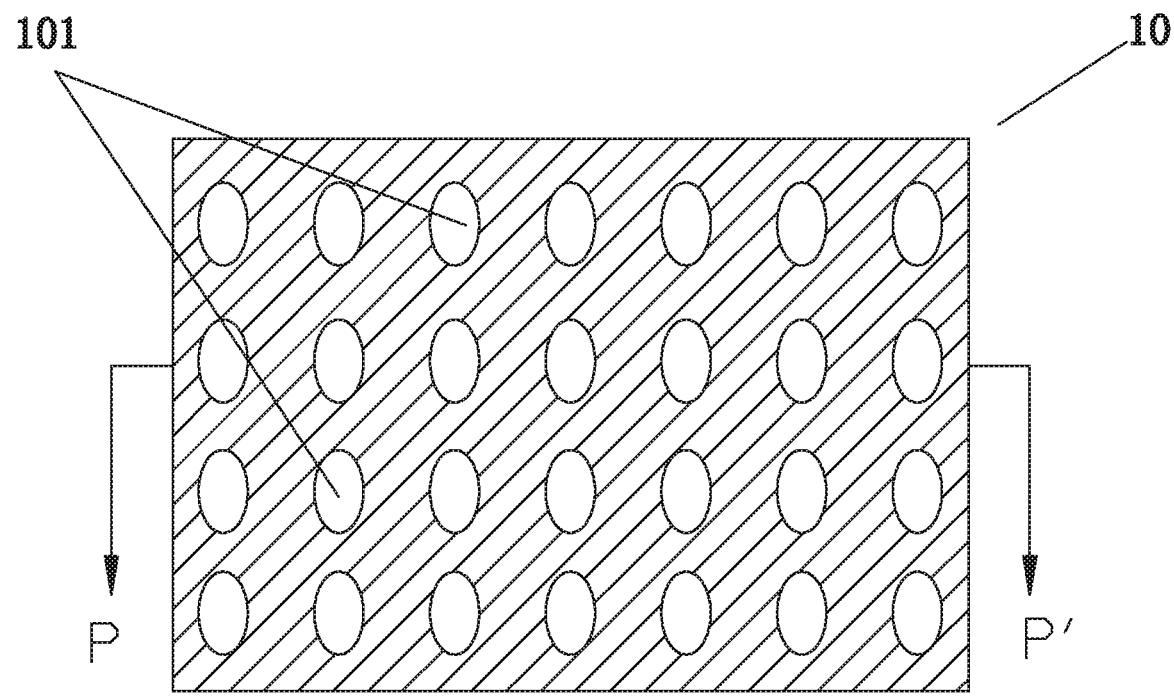
FIG. 7 is a top view of the perforated non-woven fabric of embodiment 3 of the present invention.
Figure 8:
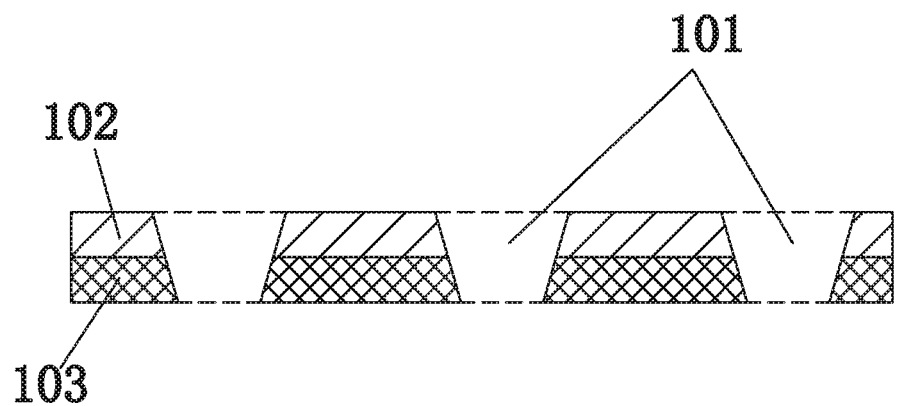
FIG. 8 is a cross-sectional view taken along the P-P' direction of FIG. 7.
Figure 9:
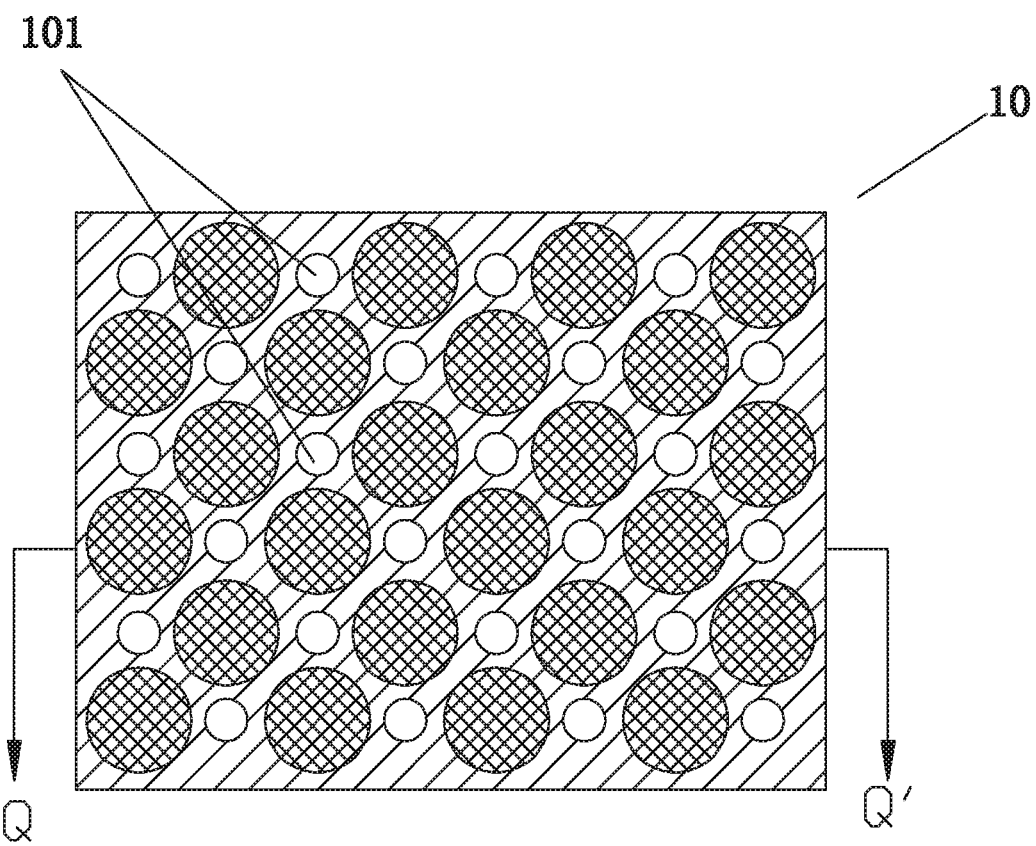
FIG. 9 is a top view of the perforated non-woven fabric of embodiment 4 of the present invention.
Figure 10:
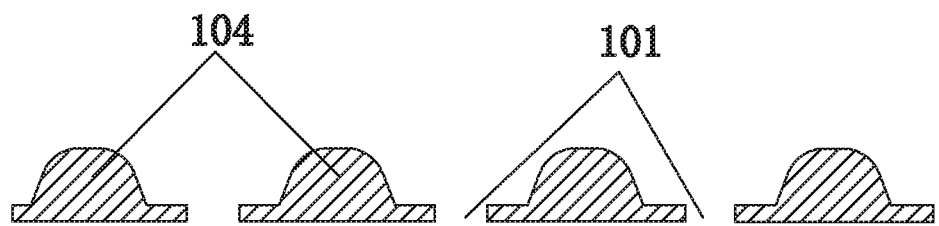
FIG. 10 is a cross-sectional view taken along the O-O' direction of FIG. 9.
Figure 11:
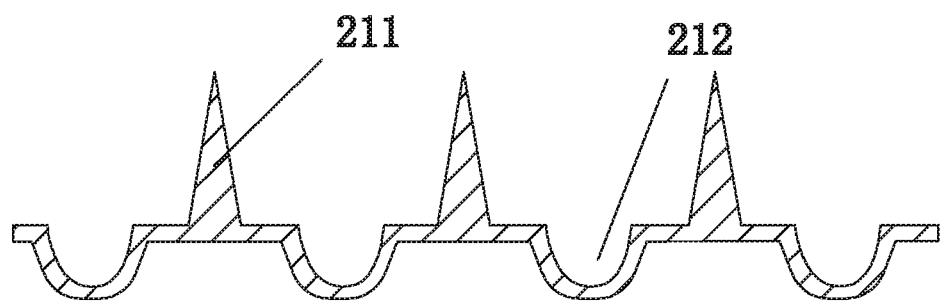
FIG. 11 is a schematic diagram of the structure of the punching pin insert and groove of the circular web rotary drum of embodiment 4 of the invention.
Figure 12:
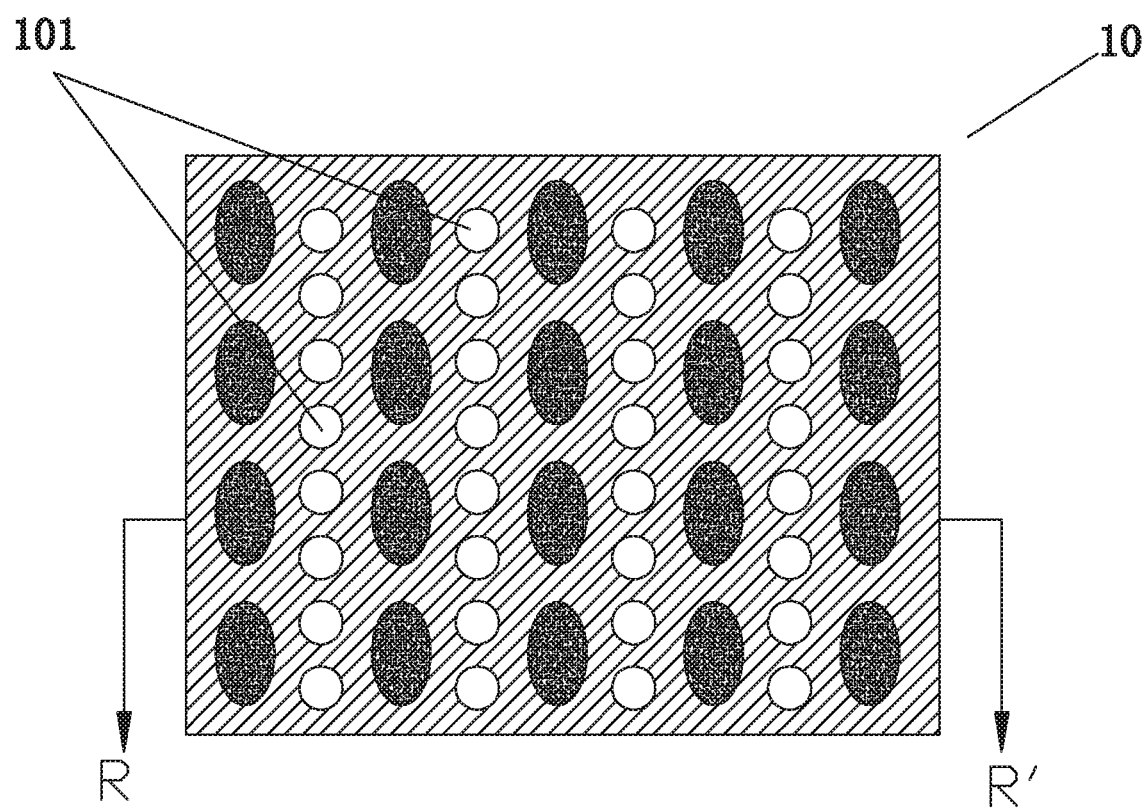
FIG. 12 is a top view of the perforated non-woven fabric of embodiment 5 of the present invention.
Figure 13:
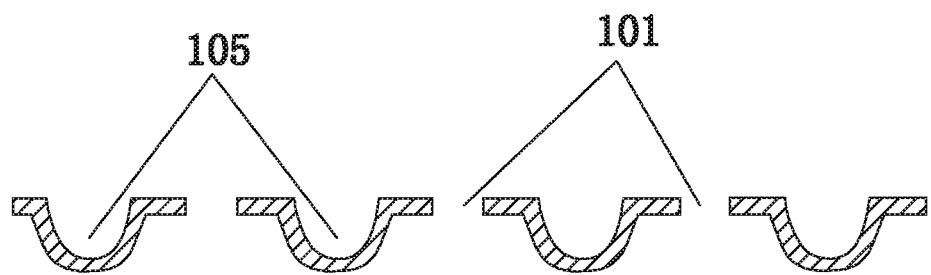
FIG. 13 is a cross-sectional view taken along the R-R' direction of FIG. 12.
Figure 14:
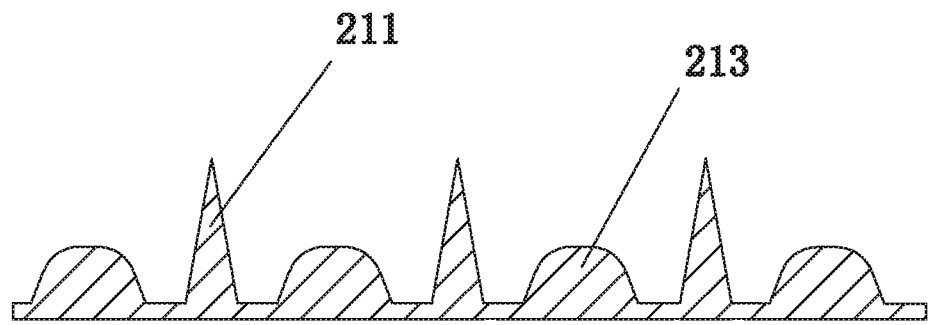
FIG. 14 is a schematic diagram of the structure of the punching pin insert and the convex of the circular web rotary drum of embodiment 5 of the invention.

As shown in FIGS. 1, 3 and 4, the hot air through non-woven fabric fibers are carding into at least one layer of fiber web through an unpacking device and a loosening device; at least one layer of fiber web is sent to a circular web rotary drum type oven 2. The surface of the circular web rotary drum 21 of the circular web rotary drum type oven 2 has a mesh hole 210 and a punching pin insert 211. The hot air of 130~200° C. in the circular web rotary drum type oven passes through the mesh hole 210 and alternately through the fiber web and consolidates it, at the same time, the punching pin insert 211 will penetrate the corresponding surface of the fiber web to form through holes 101, thereby forming the perforated non-woven fabric 10.

The perforated non-woven fabric 10 has a plurality of through holes 101, the total area of plurality of through holes 101 accounts for the 10~80% of the total area of the perforated non-woven fabric 10, the opening of the plurality of through holes 101 is flat with the surface of the perforated non-woven fabric 10, and the density of the plurality of through holes 101 on the perforated non-woven fabric 10 is $3/cm^2 \cdot 100/cm^2$, the fiber density of the edge of each of the through holes 101 is similar to or the same as the fiber density of the other regions of the perforated non-woven fabric 10, and only the fibers located on the wall surface of the through hole 101 are bonded to each other.

Since only the fiber surface layer of the wall surface of the through hole 101 is bonded at the time of molding, so that the edge region of the through holes of the non-woven fabric is not broken to form rigid breaks, or melted to form a dense fiber area or a filmed area, so that the softness of the non-woven fabric is not to be destroyed by the opening, which reduces the graininess caused by the opening and the non-woven fabric after opening is made softer than the existing perforated non-woven fabric 10. In particular, in the existing technology of opening holes with a pair of heated concave rollers and needle rolls, if the area of a single hole is larger, the hole is more difficult to shape and is to be closed easily during the winding process. However, in the present invention, since the forming process of the holes is different, the fibers only surround the through holes 101, so that the holes are not easily closed after winding, and the inner and outer hole shape the rolls are uniform. Although the opening of the perforated non-woven fabric 10 is a plane opening, it does not increase in the thickness direction of the non-woven fabric, but because the punching needle has a cylinder, cone or pyramid structure, the hole formed can be a straight hole or a funnel shaped opening. It is beneficial to collect body fluid, speed up the osmotic speed, and form a rapid osmosis channel.

The following is a test method for fiber density and softness of perforated non-woven fabric 10 obtained in the embodiment of the present invention:

the fiber density test method:

Since the perforated non-woven fabric 10 of the invention is to spread the fiber evenly on the rotary drum of a circular web oven, because the circular web rotary drum 21 has a punching pin insert 211, the fiber is formed the through holes 101 around the punching pin insert 211, so the number of fibers at the edge of the opening area and other areas without through holes 101 is the same, in the same number of fibers, the size of fiber density depends on the size of the thickness.

The fiber density can be determined by measuring the vertical distance between the edge of the hole and other regions without through holes 101 by the XTL-200 electron microscope.

The Softness Test Method:

Test instruments: Handle-o-meter (softness tester) American Thwing-Alb

Test sample: The size is 203.3 mm×203.2 mm

Test Steps:

1) Select the test slit spacing 5 mm.

2) Place the sample in the center on the instrument test platform (the center corresponds to the slit and the cross bar);

3) Press the test key to move the pressure cross bar and press the sample into the slit.

4) At this time, the display screen will display the resistance changes (including stiffness, roughness) in the test, after the test, display the maximum resistance value;

5) The positive and negative two sides and the longitudinal and transverse directions of the sample are measured respectively. The average analysis of the four measurement results is made.

Embodiment 1

As shown in FIGS. 1, 3, 4, 5 and 6, a method for manufacturing perforated non-woven fabric is described. The following steps are included:

(1) The 1.5 dtex two-component PE/PET fiber is woven into a fiber web through opening and loosening devices.

(2) The fiber web is sent to a circular web rotary drum type oven 2. The surface of the circular web rotary drum 21 of the circular web rotary drum type oven 2 has a mesh hole 210 and a punching pin insert 211. The hot air of 130~200° C. in the circular web rotary drum type oven passes through the mesh hole 210 and alternately through the fiber web and consolidates it, wherein the temperature is 130~200 C, the fan frequency is 10~50 Hz and the punching pin insert 211 will penetrate the fiber web surface to form through holes 101, thus forming the perforated non-woven fabric 10, wherein: The total area of through holes 101 is 70% of the total area of the perforated non-woven fabric 10, the shape of through holes 101 is round, and the density of through holes is 40/cm².

The top of the through holes on the perforated non-woven fabric 10 is located on the upper surface of the non-woven fabric, the bottom of the hole is located on the lower surface of the non-woven fabric and is flat with the lower surface. As the bottom of the punching pin insert 211 on the circular web rotary drum 21 is a cylinder or prism, the cross section of the top of the through holes 101 is the same as the cross section of the bottom, forming a straight hole, and the top is a cone or a pyramid, which is favorable for the fiber web to be easily peeled off the circular web rotary drum 21 after forming. The fiber density of the perforated non-woven fabric 10 is the same in the edge region of the through holes 101 and in the other regions. Under the hot air, the melting point of the double component fiber surface PE is lower and the melting point of the core layer PET is higher. At the temperature of 130-200° C., only the surface is fused and adhesion, and the fiber in the edge region of through holes 101 is only arranged around the through holes 101, so that the edge region of the through holes of the non woven fabric is not broken to form rigid breaks, or melted to form a dense fiber area or a filmed area, only the fibers surround the through holes, the fiber surface is melted and adhered to each other so that the softness of the non-woven fabric is not to be destroyed by the opening, which reduces the graininess caused by the opening and the non woven fabric after the opening is made softer than the conventional perforated non-woven fabric 10.

Handle-o-meter (softness tester) was used to test non-woven fabrics with different processing methods. The results are as follows:

| Name | Fiber component | Opening method | Softness (MD) mN | Softness (CD) mN |
|---|---|---|---|---|
| perforated non-woven | 1.5 dtex PE/PET | Needle roller and concave roller | 20 | 25 |

-continued

| Name | Fiber component | Opening method | Softness (MD) mN | Softness (CD) mN |
|---|---|---|---|---|
| fabric 101 perforated non-woven fabric 102 | 1.5 dtex PE/PET | heating punch punching | 15 | 18 |
| the perforated non-woven fabric 10 of the invention | 1.5 dtex PE/PET | Punching in a rotary web oven | 6 | 10 |

It can be seen that the soft properties of the perforated non-woven fabric 10 made by the method mentioned in this invention will not be affected by the fiber breakage or the fiber melting zone or the membrane area, thereby increasing the penetration channel and increasing the penetration time, and ensuring the soft properties of the perforated non-woven fabric 10 is good.

Embodiment 2

As shown in FIGS. 2, 3, 5 and 6, a method for manufacturing perforated non-woven fabric is described. The following steps are included:

(1) The 2.0 dtex two-component PE/PET fiber is woven into a fiber web through opening and loosening devices.

(2) The fiber web is fed into the preheating device for preheating, and the preheating temperature is 90-100 degrees ° C. The preheating device can be a heating roller or a hot air oven.

(3) The preheating fiber web is sent to a circular web rotary drum type oven 2. The surface of the circular web rotary drum 21 of the circular web rotary drum type oven 2 has a mesh hole 210 and a punching pin insert 211. The hot air in the circular web rotary drum type oven passes through the mesh hole 210 and alternately through the fiber web and consolidates it, wherein the temperature is 130~200 C, the fan frequency is 10~50 Hz and the punching pin insert 211 will penetrate the fiber web surface to form through holes 101, thus forming the perforated non-woven fabric 10, wherein: The total area of through holes 101 is 70% of the total area of the perforated non-woven fabric 10, the shape of through holes 101 is round, and the density of through holes is 40/cm².

In this embodiment, the preheating device (preheating oven) is added before the circular web rotary drum type oven, when preheating, as the surface of the fiber is made up of HDPE, the melting point of the HDPE is 130° C., so the fiber web will have a certain temperature at the preheating temperature, and the fiber will not melt, thereby, the fiber web can be accelerated in the circular web rotary drum type oven 2 for opening and shaping, further increasing the production speed of the perforated non-woven fabric, improving the production efficiency and reducing the production cost.

Embodiment 3

As shown in FIGS. 1, 3, 7 and 8, a method for manufacturing perforated non-woven fabric is described. The following steps are included:

(1). 2.0 dtex double component hydrophilic PE/PET fiber and 2.0 dtex double component hydrophobic PE/PET fiber were carded into fiber web by opening and loosening device, and then paving two layers of fiber web together into a fiber web.

(2) The two layers of fiber web is sent to a circular web rotary drum type oven 2. The surface of the circular web rotary drum 21 of the circular web rotary drum type oven 2 has a mesh hole 210 and a punching pin insert 211. The hot air of 130~200° C. in the circular web rotary drum type oven passes through the mesh hole 210 and alternately through the fiber web and consolidates it, wherein the temperature is 130~200 C, the fan frequency is 10~50 Hz and the punching pin insert 211 will penetrate the fiber web surface to form through holes 101, thus forming the perforated non-woven fabric 10, wherein: The total area of through holes 101 is 40% of the total area of the perforated non-woven fabric 10, the shape of through holes 101 is elliptic, and the density of through holes is 30/cm$^2$.

The perforated non-woven fabric in this embodiment consists of 10 two layers of fiber web. The top of the through holes 101 is located on the upper surface of the non-woven fabric. The bottom of the hole is located on the lower surface of the non-woven fabric and is flat with the lower surface. As the bottom of the punching pin insert 211 on the circular web rotary drum 21 is a cone or pyramid, the cross section of the top of the through holes 101 is larger than the cross section of the bottom, forming a funnel-shaped opening, which is beneficial to the absorption of body fluid and the prevention of liquid backflow. The fiber in the edge area of through holes 101 only arranged around through holes 101, and the fiber is not broken to form rigid breaks or melted to form a dense fiber area or a filmed area, so that the softness of the non-woven fabric is not to be affected. At the same time, the upper layer 102 of the perforated non-woven fabric 10 in this embodiment is a hydrophobic fiber layer, and the lower layer 103 is the hydrophilic fiber layer, which can reduce the residual body fluid in the upper layer of the 102 fiber layer, and can effectively prevent the body fluid from the lower layer 103 back to the surface of the perforated non-woven fabric 10, so as to achieve the purpose of drying.

Embodiment 4

As shown in FIGS. 1, 3, 9, 10 and 11, a method for manufacturing perforated non-woven fabric is described: The following steps are included:

(1) The 1.5 dtex two-component hydrophile PE/PET fiber is woven into a fiber web through opening and loosening devices.

(2) The fiber web is sent to a circular web rotary drum type oven 2. The surface of the circular web rotary drum 21 of the circular web rotary drum type oven 2 has a mesh hole 210 and a punching pin insert 211 and the groove 212. The hot air of 130~200° C. in the circular web rotary drum type oven passes through the mesh hole 210 and alternately through the fiber web and consolidates it, wherein the temperature is 130~200 C, the fan frequency is 10~50 Hz and the punching pin insert 211 will penetrate the fiber web surface to form through holes 101, the fiber web forms a convex 104 in the groove 212 of the circular web rotary drum 21, thus forming the perforated non-woven fabric 10, wherein: The total area of through holes 101 is 25% of the total area of the perforated non-woven fabric 10, the shape of through holes 101 round, and the density of through holes is 25/cm$^2$.

The difference between this embodiment and embodiment 1 is in that: The surface of the circular web rotary drum 21 is provided with a number of grooves 212. The grooves 212 are spaced with the punching pin insert 211. The grooves 212 may be hemispherical.

After the perforated non-woven fabric entering the groove 212 in the fiber web in the embodiment, the fiber will be evenly distributed in the groove 212. Under the hot air, the fibers are bonded to each other to form non-woven fabrics, and the fibers located in the groove 212 form a convex 104 on the perforated non-woven fabric 10. Compared with the convex formed by a pair of heated concave-convex rolls in the prior art, the convex 104 has a fiber-dense area formed by extrusion without fiber on the surface and a film-forming area formed by fiber melting, so the convex 104 is softer and more skin-friendly, and can also reduce the area of contact with the skin in use and feel more dry.

Embodiment 5

As shown in FIGS. 3, 12, 13 and 14, a method for manufacturing perforated non-woven fabric is described: The following steps are included:

(1) The 2.0 dtex two-component hydrophilic PE/PET fiber is woven into a fiber web through opening and loosening devices.

(2) The fiber web is sent to a circular web rotary drum type oven 2. The surface of the circular web rotary drum 21 of the circular web rotary drum type oven 2 has a mesh hole 210 and a punching pin insert 211 and the convex part 213. The hot air of 130~200° C. in the circular web rotary drum type oven passes through the mesh hole 210 and alternately through the fiber web and consolidates it, wherein the temperature 130~200 C, the fan frequency is 10~50 Hz and the punching pin insert 211 will penetrate the fiber web surface to form through holes 101, the fiber web forms a concave part 105 in the convex part 213 of the circular web rotary drum 21, thus forming the perforated non-woven fabric 10, wherein: The total area of through holes 101 is 28% of the total area of the perforated non-woven fabric 10, the shape of through holes 101 is round, and the density of through holes is 35/cm$^2$. The shape of the concave part is ellipse, round, polygon or other irregular shape.

The difference between this embodiment and embodiment 4 is that the surface of the circular web rotary drum 21 has a convex part 213, and the convex part 213 is spaced with the punching pin insert 211.

When the perforated non-woven fabric 10 in the embodiment enters the circular web rotary drum 21 in the fiber web, the fiber is arranged evenly around and on the top of the convex part 213 due to the presence of the convex part 213. Under the hot air, the fibers are bonded to each other to form non-woven fabrics, and the fibers in the convex part 213 form the concave part 105 on the perforated non-woven fabric 10, and the concave part 105 can store the liquid when the body fluid or the baby's soft stool reaches the said perforated non-woven fabric 10, preventing side leakage and skid leakage, thus helping to penetrate and absorb and reach the dry purpose.

The above mentioned is only a better embodiment of the invention. Therefore, the scope of the invention can not be limited, that is, the equivalent changes and modifications made according to the scope and contents of the patent of the invention shall still belong to the scope covered by this invention.

INDUSTRIAL APPLICABILITY

The perforated non-woven fabric and its manufacturing method, the edge region of the through holes of the non woven fabric is not broken to form rigid breaks, or melted to form a dense fiber area or a filmed area, only the fibers surround the through holes, the fiber surface is melted and adhered to each other so that the softness of the non-woven fabric is not to be destroyed by the opening, which reduces the graininess caused by the opening.

The invention claimed is:

1. A method for manufacturing a perforated non-woven fabric comprising at least one fiber layer, wherein:
   the at least one fiber layer comprises a plurality of through holes,
   openings of the plurality of through holes are flat with a surface of the perforated non-woven fabric,
   a fiber density at an edge of each through hole of the plurality of through holes is the same as a fiber density in other areas of the perforated non-woven fabric,
   only surfaces of fiber of the at least one fiber layer disposed at inner sides of the plurality of through holes are bonded to each other,
   the method comprises:
      carding the fiber into at least one layer of fiber web through an unpacking device and a loosening device, and
      sending the at least one layer of fiber web to a circular web rotary drum type oven,
   a surface of a circular web rotary drum of the circular web rotary drum type oven comprises a mesh hole and a punching pin insert,
   the circular web rotary drum defines an outer surface, and
   the at least one layer of fiber web covers more than half of the outer surface of the circular web rotary drum in a circumferential direction of the circular web rotary drum, hot air of 130-200° C. in the circular web rotary drum type oven perpendicularly passes through the mesh hole and through the more than half of the outer surface and consolidates the at least one layer of fiber web and, at the same time, the punching pin insert penetrates a corresponding surface of the at least one layer of fiber web to form the plurality of through holes, thereby forming the perforated non-woven fabric.

2. The manufacturing method according to claim 1, wherein the punching pin insert is conical, cylindrical, or pyramidal.

3. The manufacturing method according to claim 1, wherein:
   the circular web rotary drum comprises a number of convex inserts,
   the convex inserts form concave parts in the perforated non-woven fabric, and
   the perforated non-woven fabric with the plurality of through holes and the concave parts formed by integral molding.

4. The manufacturing method according to claim 1, wherein:
   the circular web rotary drum comprises a number of grooves,
   the grooves form convex parts in the perforated non-woven fabric, and
   the perforated non-woven fabric with the plurality of through holes and the convex parts formed by integral molding.

5. The manufacturing method according to claim 1, wherein the method comprises:
   preheating the at least one layer of fiber web to 90-100° C. by a preheating device, and
   placing the at least one layer of fiber web in the circular web rotary drum type oven after the preheating.

6. The manufacturing method according to claim 5, wherein the preheating device is a preheating oven.

7. The manufacturing method according to claim 1, wherein a total area of the plurality of through holes accounts for 10-80% of a total area of the perforated non-woven fabric.

8. The manufacturing method according to claim 1, wherein a density of the plurality of through holes on the perforated non-woven fabric is $3/cm^2$-$100/cm^2$.

* * * * *